United States Patent [19]

Cobb

[11] Patent Number: 4,770,042
[45] Date of Patent: Sep. 13, 1988

[54] SUSPENSION STABILITY MONITORING APPARATUS

[75] Inventor: Wesley N. Cobb, University Heights, Ohio

[73] Assignee: The Standard Oil Company, Cleveland, Ohio

[21] Appl. No.: 139,178

[22] Filed: Dec. 24, 1987

Related U.S. Application Data

[63] Continuation of Ser. No. 944,326, Dec. 18, 1986, abandoned.

[51] Int. Cl.[4] .......................................... G01N 29/02
[52] U.S. Cl. .................................. 73/597; 73/32 A; 73/61.4
[58] Field of Search ................. 73/597, 32 A, 61.4, 73/61 R

[56] References Cited

U.S. PATENT DOCUMENTS

| | | |
|---|---|---|
| 2,668,365 | 2/1954 | Hogin . |
| 2,978,899 | 4/1961 | Kritz ................................. 73/24 |
| 3,028,749 | 4/1962 | Welkowitz ..................... 73/32 A |
| 3,514,217 | 5/1970 | Reiss . |
| 3,529,153 | 9/1970 | Zimmerman et al. . |
| 3,648,513 | 3/1972 | Patterson ..................... 73/597 X |
| 3,896,660 | 7/1975 | Valentyik ....................... 73/61.4 |
| 3,911,726 | 10/1975 | Georgiev ...................... 73/32 A |
| 4,007,319 | 2/1977 | Weisser et al. ................. 526/60 |
| 4,022,053 | 1/1977 | Hayakawa ................... 73/32 R |
| 4,041,502 | 8/1977 | Williams et al. ............. 346/33 A |
| 4,140,007 | 2/1979 | Bosland et al. .................. 73/61.4 |
| 4,235,099 | 11/1980 | Ishizaka ........................ 73/32 A |
| 4,261,196 | 4/1981 | Scheid, Jr. .................... 73/32 R |
| 4,297,608 | 10/1981 | Jensen ............................ 310/335 |
| 4,414,841 | 11/1983 | Porenski, Jr. et al. ........... 73/61 R |
| 4,442,700 | 4/1984 | Swoboda ....................... 73/32 A |
| 4,506,541 | 3/1985 | Cunningham ................ 73/32 R |
| 4,522,068 | 6/1985 | Smith ............................ 73/597 X |
| 4,527,420 | 7/1985 | Foote ............................ 73/61 R |

FOREIGN PATENT DOCUMENTS

| | | | |
|---|---|---|---|
| 476498 | 1/1976 | U.S.S.R. ......................... 73/61 R |
| 1185224 | 10/1985 | U.S.S.R. ........................... 73/597 |

OTHER PUBLICATIONS

Chen, C. et al. *Three-Transducer Differential Phase-Shift Method for Measurement of Ultrasonic Velocity in Liquids*, In Rev. Sci. Instr., vol. 46(8): pp. 1095-1098, Aug. 1975.

Primary Examiner—Stewart J. Levy
Assistant Examiner—Joseph W. Roskos
Attorney, Agent, or Firm—Dilworth & Barrese

[57] ABSTRACT

Suspensions, emulsions and the like are monitored with apparatus which pulses ultrasonic waves through a suspension at elevations from bottom to top along a column of such suspension to determine if there has been alteration in the original composition thereof, the apparatus being particularly adapted for determining the stability of coal-aqueous slurries.

14 Claims, 3 Drawing Sheets

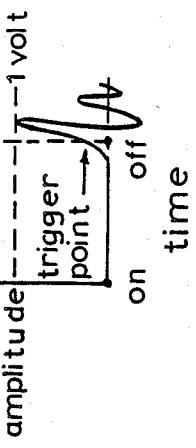
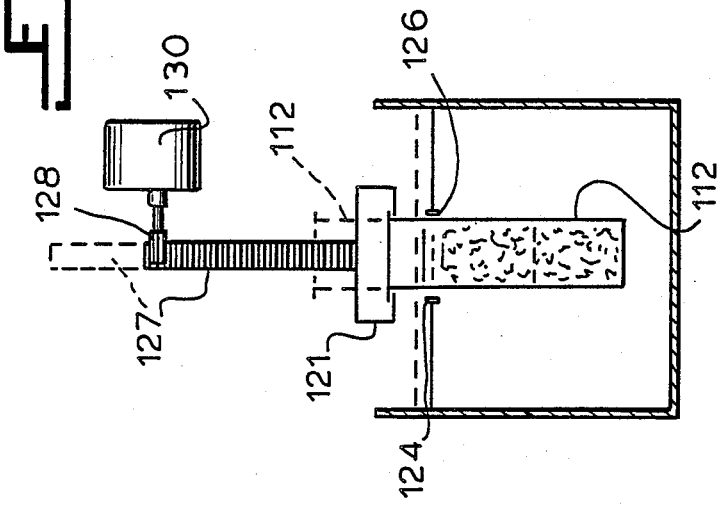
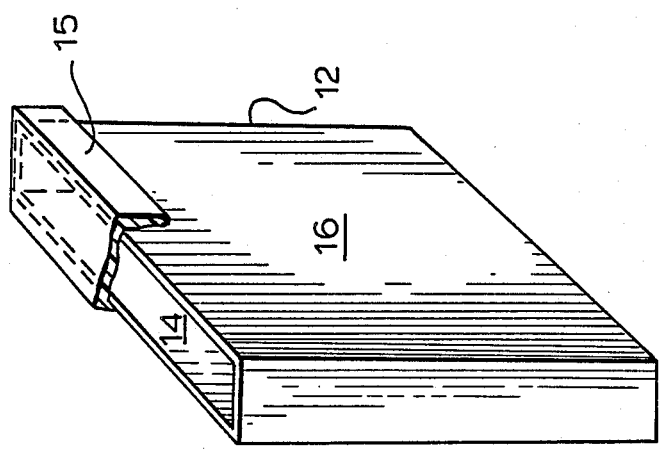

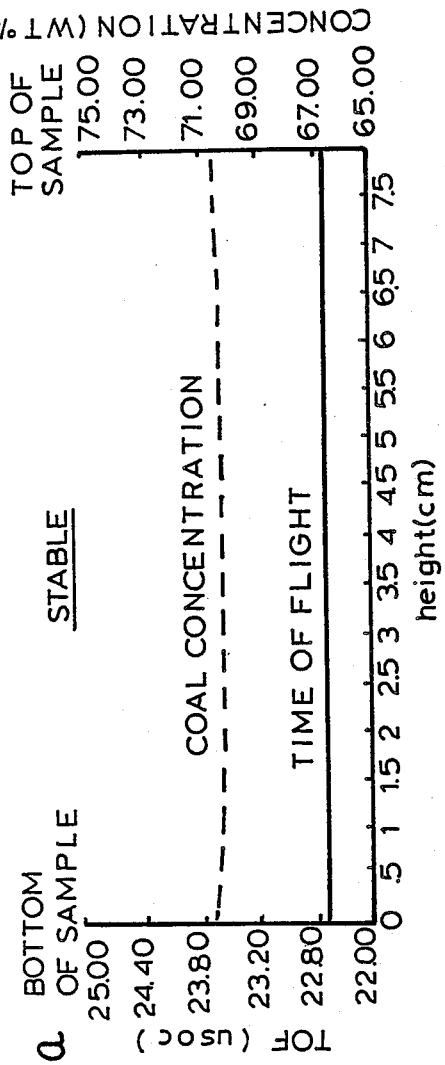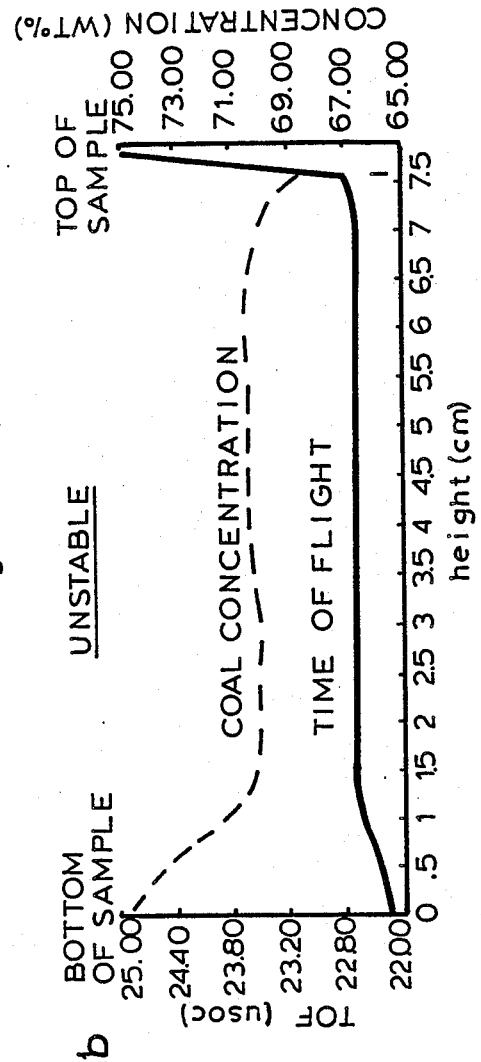

SUSPENSION STABILITY MONITORING APPARATUS

This is a continuation of co-pending application Ser. No. 944,326 filed on Dec. 18, 1986, now abandoned.

BACKGROUND OF THE INVENTION

The present invention relates to apparatus for the monitoring of suspensions, liquid emulsions, mixtures and the like to determine if change in relative component concentration has occurred therein. It is particularly applicable to the monitoring of coal-aqueous slurries to determine if coal settlement has taken place in such slurries.

It is important that certain characteristics of liquids, suspensions and the like be monitored for various purposes. For that reason certain monitoring techniques and apparatus by which monitoring can be effected heretofore have been developed. For example, U.S. Pat. No. 4,041,502 describes measuring sedimentation in blood samples by passing light wave energy through a glass tube enclosed column of the sample and recording that signal in such manner as to provide a plot of the changing location within the sample of the separation boundary between blood cells and clear plasma fluid. U.S. Pat. No. 4,442,700 uses a device for ultrasonic wave pulsing through the casing of a lead-acid battery to determine specific quantity (density) of the electrolyte therein and hence indication of the serviceability of the battery. U.S. Pat. Nos. 3,028,749 and 3,911,726 also describe ultrasonic procedures for determining various parameters, e.g., density, of liquids as does U.S. Pat. No. 4,235,099 which relates to apparatus particularly useful for liquids specific gravity mensuration in medical and related activities. U.S. Pat. No. 4,007,319 describes use of electrical conductance for monitoring a suspension polymerization reaction so as to anticipate for corrective counteraction thereto, of the onset of reaction conditions that signal incipient failure of suspension formation.

Other patents which deal with aspects of product monitoring as related to density, sedimentation and analogous considerations include U.S. Pat. Nos. 2,668,365; 2,715,831; 2,825,698; 2,978,899; 3,514,217; 3,529,153; 3,896,660; 3,964,037; 4,007,315; 4,002,053; 4,041,500; 4,047,891; 4,048,844; 4,140,007; 4,261,196; 4,297,608; 4,466,272; 4,487,278; 4,506,541 and 4,527,420.

Those skilled in the art readily understand the wide range of potential applications for suspension, emulsion and mixture monitoring in various industries such as food, pharmaceuticals, minerals processing, waste treatment, paper, etc. Another area of special applicability for such monitoring is in respect to coal fuels wherein the ready facility for monitoring coal slurries used, e.g., for fuel purposes is desirable so that determination of optimized thickener and surfactant amounts to be added to a fuel slurry at production thereof to insure long term stability, are ascertainable. U.S. Pat. No. 4,441,889 describes a coal-in-aqueous slurry form wherein additive materials such as surfactants, stabilizing agents, thickeners, etc., are employed to disperse and stabilize the coal to high solids concentrations of 70% by weight, or higher. These mixtures are free-flowing, have excellent long term storage stability and being in fluid form, can be burned in apparatus normally used for burning fuel oil. Since these coal-aqueous slurries generally will be stored for some time prior to use for their intended purposes any sedimentation which might occur therein would be undesirable when the mixture was later used in a fuel burning operation such as in a boiler. By monitoring over a period of time representative samples of the slurries taken from production runs, the long term stability of the slurries are learned as is data useful for compensating in future production for any instability noted in monitored prior produced coal-aqueous slurries of given coal solids concentration.

It is therefore desirable that a highly effective, yet simple apparatus be provided with which the solids concentration of coal-aqueous slurries and the like can be monitored on an ongoing basis and by non-destructive procedure and under the natural conditions which such slurries subsist from time of production until ultimate end use thereof.

SUMMARY OF THE INVENTION

An object of the invention is to provide apparatus for monitoring the stability of solids-containing suspensions, liquid emulsions, etc., and particularly for monitoring the stability of coal-aqueous slurries.

Another object of the invention is to provide apparatus for monitoring the stability of solids-containing suspensions, liquid emulsion, etc., in manner non-destructive of the suspension and wherein the monitoring is of a representative suspension sample drawn at production from an industrial production run so that data obtained from the sample is reflective of the stability character of the industrial suspension stocks.

A further object is to provide a suspension stability monitoring method wherein the sample is confined in a holder or sample container, monitored with ultrasonic transmitter and receiver means which is moved relative to the full height of the suspension column to obtain data at the various column elevations all this being done in a matter of a minute or so to obtain the data and then the sample conveniently stored in its holder for further monitoring at subsequent times, the foregoing being carried out without any destructive effect on the sample or causative of any change in character of the suspension.

Another object is to provide suspension monitoring apparatus which provides a visual readout display of the suspension condition.

In accordance with the invention, the apparatus includes a container wherein the solids-containing suspension in requisite sample quantity thereof can be confined, the container being made of material having good sonic transmissivity. It also includes means defining a liquid bath in which the container is disposed on a suitable support, the liquid being one having a density substantially near or at that of the suspension, e.g., water and with the bath level above the suspension column surface level. A transmitting transducer is positioned at one side of the holder and a receiving transducer at an opposite side, the two transducers being mountingly connected to a vertically moveable head to allow for unitary vertical movement of the two up and down alongside the holder and upon vertically reciprocating the head with suitably connected head drive means (alternatively, the transducers could be fixed in the bath below its level and the holder could be vertically moved). Ultrasonic waves are pulsed through the suspension by the transmitting transducer as it is moved between the two vertical extremes of the suspension column and these waves are detected by the receiving transducer after they have passed through the suspension, the initiation of a pulse starting a timer/counter unit. The detected sound waves are converted to electrical signals indicative of the sonic wave time-of-flight through the suspension and bath by suitable circuit components including an automatic gain control circuit and timer/counter unit and includes the feature of effecting timer/counter unit stopping by a threshold voltage value of said signals.

Since the time-of-flight of sound waves propagated through a stable suspension of a given solids concentration such as a 70% coal solids coal-aqueous slurry can be determined, this data serves as a comparative to which the electrical signals obtained from the sample can be applied such as an acquisition by a microprocessor and thus deviation therefrom noted as a comparative resolution in the microprocessor so that deviation would signal alteration of the solids concentration from a desired level, i.e., occurrence of sedimentation. This comparison then can be displayed in convenient form such as in a visual plot display, digital display, etc., controlled by the microprocessor. Where visual plot of the time-of-flight data from bottom to top of the column is employed, presence of or lack of linearity in the plot is indicative of the stable or unstable condition of the coal-aqueous slurry.

The testing of the sample can be carried out very quickly in about one minute inasmuch as a sample column of (preferably a rectangular section column) about ¼ to ½ inch depth, 4 inch width and height of about 3 to about 4 inches is all that is needed.

The invention accordingly comprises the features of construction and arrangements of parts as embodied in apparatus for monitoring the stability of suspensions as will be exemplified in the description hereinafter set forth and the scope of the invention will be indicated in the claims.

BRIEF DESCRIPTION OF THE DRAWINGS

A fuller understanding of the nature and objects of the invention will be had from the following detailed description taken in conjunction with the accompanying drawings, in which:

FIG. 2 is a perspective view of the sample container in which the suspension to be monitored is confined, the sample when not being monitored being left stored in such container, the container cover being shown broken away;

FIG. 3a is a visual display plot showing time-of-flight and coal concentration values as obtained along various bottom to top levels in a sample column of a stable coal-aqueous slurry containing a 70% coal concentration which was stored for a period after draw off from a production run;

FIG. 3b is a like plot of an unstable coal-aqueous slurry sample obtained from monitoring such sample after the same storage period and this sample having been obtained from another production run;

FIG. 4 is a graph showing the threshold voltage at which the timer/counter operation is stopped; and FIG. 5 is a fragmentary schematic showing of the alternative arrangement wherein the transducers are fixed in the bath and the suspension holder is moved during the monitoring.

Throughout the description like reference numerals ar used to denote like parts in the drawings.

DESCRIPTION OF THE PREFERRED EMBODIMENT

Figure 1:
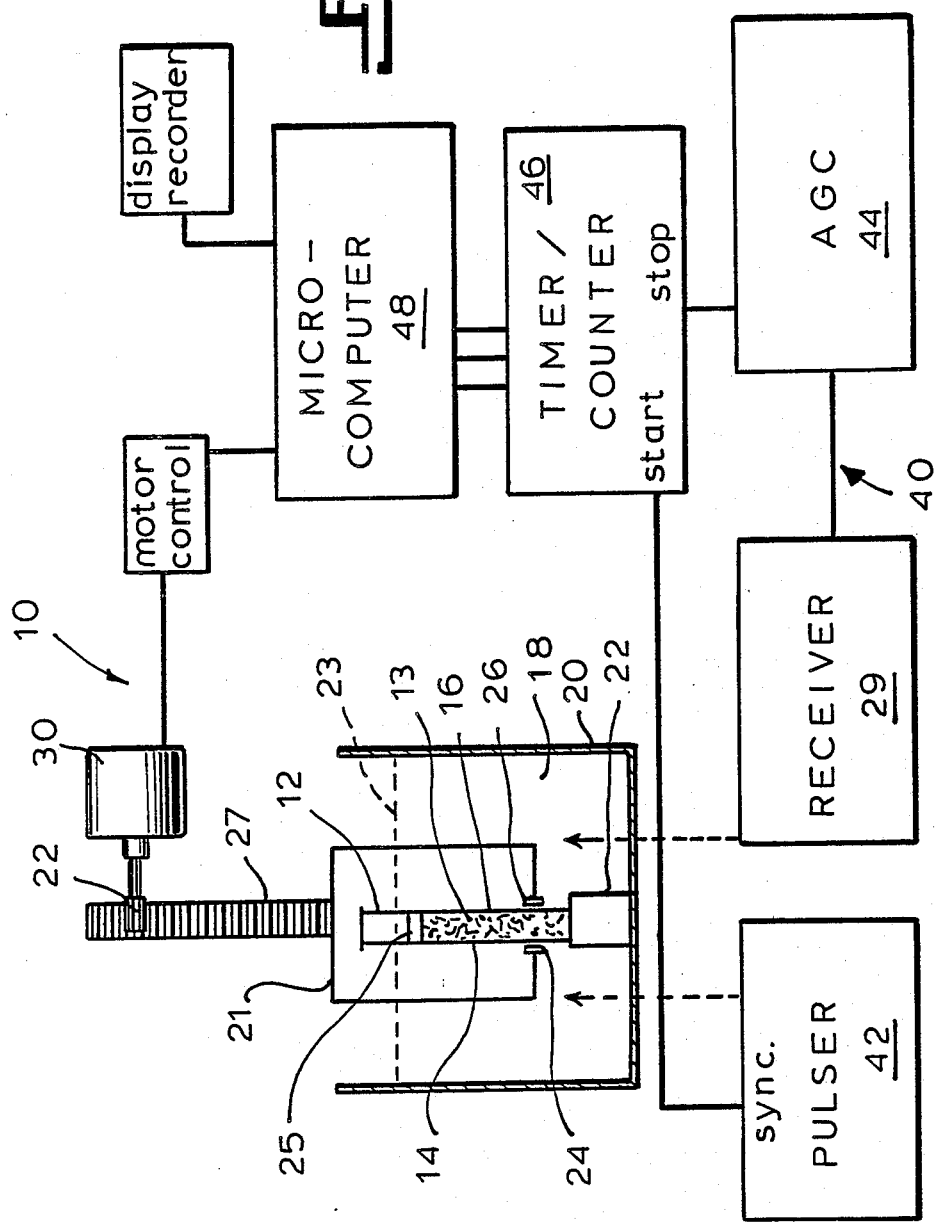
FIG. 1 is a schematic showing of apparatus with which solids-containing suspensions can be monitored in accordance with the principles of the present invention and wherein the sample is held fixed in the liquid bath and the transducers are moved up and down alongside the sample holder.

The apparatus 10 shown in FIG. 1 can be used in practicing the monitoring method described and claimed in the commonly owned, concurrently filed application of Wesley N. Cobb et al. Ser. No. 944,338 entitled "Monitoring The Suspension Stability Of Solids-Containing Suspensions And The Like" the disclosure of which is hereby incorporated by reference.

The apparatus 10 includes a sample holder or container 12 wherein a sample column 13 of coal-aqueous slurry which sample had been drawn from a production run source of slurry can be confined, the holder having a readily snap-fit removeable cover 15. The coal solids concentration of the sample can have a value, e.g., of 70% although it will be understood that such product can be made with various and other intended coal solids concentrations. The sample in the container 12 is intended to be stored, monitored, returned to storage in the self-same container without any disturbance thereto, monitored again, etc., for as long as it can be expected that the production run commercial product material may subsist in storage until put to final end use so that the ongoing monitoring of the sample is reflective of the stability condition of the commercial product.

The container 12 preferably is made of a thermoplastic material to provide good sonic transmissivity, glass, e.g., not being as acoustically transparent as most thermoplastics. One form of thermoplastic suited for this purpose is polypropylene. The use of thermoplastic allows the passage of ultrasonic waves through the holder without great attenuation or reflection thereof and thereby lessens interference with the clear reception of sonic signals passing through the suspension. The holder can as shown in FIG. 2, be of rectangular profile having, e.g., spaced parallel side walls 14, 16 which measure about 5" high, slightly more than 4" wide, and slightly more than ½" in depth so that a coal slurry column about 4"×3" by about ¼" to ½" can be confined therein. For monitoring purposes a relatively narrow depth sample and of about 250 milliliters total volume is all that is required for effective and reliable monitoring.

The sample containing holder 12 is placed in a liquid bath 18, the bath being contained in a suitable vessel 20 and the holder supported in suitable manner as on pedestal 22 although any other types of container support could be used. The arrangement is such that the bath level 23 is above the sample level 25. The bath 18 is selected to be a liquid having a density substantially near or at that of the coal aqueous slurry and conveniently can be water. An important aspect of the invention is that monitoring is carried out under consistent conditions so that there is no false signal data obtained as for example where varying monitoring temperature conditions could exist. Maintenance of constant sample, bath and test space temperatures is readily controlled.

A sonic head frame or vertically moveable head 21 carries on depending structure thereof, a transmitting transducer 24 and a receiving transducer 26, these two devices being disposed adjacent the respective two side walls 14, 16 of the container and being reciprocally aligned one with the other. Head 21 is fixed to means with which the frame can be reciprocated or straight line vertically moved up and down to allow for ultrasonic monitoring of the coal aqueous slurry sample at various elevations therein between the two vertical extremes thereof. Such means could be a rack 27 attached to the head frame and in mesh with pinion 28, the pinion being driven by a control motor 30 that reversibly drives the pinion to produce the required up and down movement of the head. FIG. 5 depicts an alternative arrangement wherein holder 112 is supported on a head frame 121 and the transducers 124, 126 are held fixed a submerged locations in the liquid bath. When motor 130 rotates pinion 128, rack 127 and hence the sample holder is moved upwardly or downwardly and in this manner the monitoring of the sample at succeeding vertical levels therein takes place.

In FIG. 1, the operative control arrangement for the apparatus is shown in block diagram form generally at 40. Pulse generator 42 is used to energize transmitting transducer 24 so that device generates short duration (e.g., 1 microsecond) ultrasonic waves that pass through the sample 13 and bath medium between the transducers and are received by the receiving transducer 26 so that these receptions are converted to electrical signals which as output from receiver 29 are fed to an automatic gain circuit 44. The automatic gain circuit 44 serves to limit the received signal voltage to an amplitude of, e.g., one volt to compensate for any ultrasonic attenuation changes in the sample. If the received signal was not compensated, the time at which the attenuated received signal exceeded the threshold signal (as described below) would change with signal amplitude (attenuation) resulting in errors in time-of-flight measurements of the sonic wave travel through the suspension. Upon initiation of each sound pulse by transducer 24, timer/counter unit 46 starts counting and when the sound pulse is received by transducer 26 and the converted electrical signal therefrom exceeds a set or threshold value (e.g., 0.1 volt), the timer/counter 46 is stopped, the interval between start and stop being the time-of-flight of the pulsed sound wave through the sample and bath medium between the transducers. FIG. 4 shows the importance of compensating for voltage amplitude so that early threshold voltage value is achieved.

To monitor change in suspension concentration due to instability, the travel time of the ultrasonic waves through the sample is measured. If the components of the suspension (e.g. coal in water) have different characteristic sound speeds, the travel time through each component will be different. Thus the measured travel time for the sample is a function of the sound speeds of the components and the relative concentrations. Suspension concentration (e.g. coal percent) can be measured by monitoring the time of flight through the sample. Microprocessor unit 48 acquires this time-of-flight data and processes same to provide time-of-flight and/or solids-concentration information, e.g., as a control output which serves to operate a visual recording or display device 60 representing time-of-flight and/or solids concentration in plot form as shown in FIGS. 3a and 3b.

In monitoring the sample, it is required to determine if any solids concentration changes due to settling have occurred at any location therein so that monitoring is carried out along the entire vertical expanse of the sample column. For that reason, the monitoring procedure will be started at one end, preferably the bottom end, of the sample. Microprocessor unit 48 can be employed to control the drive of motor 30 (through a suitable control unit) to operate movement of the sonic head frame 21 upwardly from the bottom to the top of the column in a time period of about one minute and during which period monitoring will be taking place at successive ones of elevations in the coal aqueous slurry between zero and maximum (sample level) elevations thereof. The time-of-flight information retrieved at these successive ones of the elevations indicate concentration and such data can be employed to plot the stability condition of the coal aqueous slurry sample at the various elevations. Linearity of the plot or a lack thereof provides immediate visual graphic display of stability.

In regard to simply and effectively ascertaining the coal aqueous slurry concentration of samples, the graphic plot procedure in FIGS. 3a and 3b optimizes this end. Thus in the plot recorder controlled by microprocessor output signals, time-of-flight data and aqueous slurry coal concentrations are reproduced to represent ordinates of the plot while the abscissa represents various height levels in the sample from bottom to top. These data therefore provide the most graphic indication of a particular sample condition inasmuch as the plotted data for coal concentration and time-of-flight need only be compared to the straight line abscissa as a reference datum and the closeness or departure of the plotted data with the abscissa in linearity shows sample condition.

The concentration measurements are obtained from processed time-of-flight data using the following formula:

$$\text{Solids Conc.}_l = A \cdot TOF_l + B$$

where TOF is the time-of-flight data, A is a slope calibration factor and B is an intercept calibration factor. These calibration factors are determined by obtaining TOF measurements for several stable samples of know concentration. On a plot of concentration data (Y axis) versus TOF data (X axis), A is the slope of the best fit straight line to the measurements; B is the value of the concentration where the line intercepts the concentration axis.

FIGS. 3a and 3b show respective plots of stable (initial approximity 70% solids) and unstable (initially approximately 67% solids) coal aqueous slurry samples each stored at the same time and then monitored for stability one day later. The FIG. 3a stable sample plot shows substantial linearity in both the time-of-flight and coal concentrations curves and constancy of these values therefor at all elevations in the coal aqueous slurry sample from bottom to top thereof. The FIG. 3b plot on the other hand shows that significant settling already has taken place in that sample. Thus it will be seen that a layer of high solids concentration (about 75%) has formed at the bottom of the sample as compared to the initial 67% solids concentration value. In addition, the low solids concentration at the top of the sample indicates the formation of a low-solids, surface water layer of about 0.5 cm height in the sample.

Continued and subsequent monitoring of samples can be carried out. For example, continued monitoring of the FIG. 3a sample could be carried out during successive periods of days and weeks to confirm the indicated stable character of that coal aqueous slurry. The FIG. 3b sample also could be subsequently monitored to ascertain the rate of sedimentation happening since that data then becomes useful in terms of how like compositioned production run coal aqueous slurry can more effectively be stabilized with additives, etc., at the time of production to prevent sedimentation occurring during the expected coal aqueous slurry subsistence before final end use thereof.

An important advantage of the invention is the facility with which samples can be monitored, returned to storage and subsequently monitored again. The samples once placed in the container 12 need not be disturbed since they remain in the container for monitoring under the same natural conditions applicable to commercial product storage.

While there is above disclosed only certain embodiments of the present invention it will be apparent that variations made be made therein by those skilled in the art without departing from the scope of the inventive concept disclosed.

What is claimed is:

1. Apparatus for monitoring the stability of a solids-containing suspension or the like to determine if the solids concentration thereof has altered from a desired value due to settlement of solids within the suspension, said apparatus comprising in combination a sample container for holding a column of the suspension to be monitored, said container having relatively narrow depth as compared to the width and height thereof, means defining a liquid bath in which the container can be disposed, means disposed submerged in said bath at one side of said container for transmitting ultrasonic waves through the suspension, means disposed submerged in said bath at the other side of said container for detecting ultrasonic waves after they have passed through the suspension and converting the wave detections to electrical signals indicative of wave time-of-flight through the suspension, means for effecting vertical relative movement between said ultrasonic wave transmitting and detecting means and said container so that transmission and detection of waves occurs at a succession of elevations between the vertical extremes of the suspension column to obtain time-of-flight data as electrical signals at such elevations, means comprising a microprocessor for acquiring said electrical signs for comparing said signals with known values of same representing desired solids concentrations to determine if settlement indicative deviation of such signals from the known values exits, and visual display means controlled by said microprocessor for providing output display of said electrical signals, said visual display means being a graphic plotting means generating a plot of time-of-flight and/or solids concentration values, the graphic plotting means being operable to record said signals at ordinate graph locations in correspondence to abscissa locations associated with the successive column elevations and therewith generate a line plot, the presence or absence of linearity in said line plot as compared to a straight line absicssa datum denoting respective stable/unstable conditions.

2. The apparatus of claim 1 in which the wave transmitting and detection means are mounted on a vertically moveable head, the vertical relative movement means including a drive unit connected to said moveable head for vertically reciprocating same, the sample container being supported stationary in the liquid bath with the suspension level below the bath level.

3. The apparatus of claim 2 in which the drive unit includes a drive motor and means connecting said motor to said moveable head.

4. The apparatus of claim 1 in which the wave transmission and detection means are fixed in said bath, the sample container being carried on a vertically moveable support head, the vertical relative movement means including a drive unit connected to said support head for vertically reciprocating same.

5. The apparatus of claim 4 in which the drive unit includes a drive motor and means connecting said motor to said support head.

6. The apparatus of claim 1 in which the container is made of thermoplastic material.

7. The apparatus of claim 1 in which the container is sized to contain a suspension column of about 250 milliliters.

8. The apparatus of claim 1 in which the container is sized such as to contain a suspension column with a depth thereof of about $\frac{1}{4}$ to about $\frac{1}{2}$ inch.

9. The apparatus of claim 1 in which the liquid in the bath is water and the suspension is a coal-aqueous slurry.

10. The apparatus of claim 1 in which said microprocessor controls operation of the vertical relative movement means.

11. The apparatus of claim 1 in which the means for converting wave detections to electrical signals includes a timer/counter electrically connected to the transmitting means to start timing operation at initiation of wave transmission and to the wave detecting means to stop the timing operation when the detecting signal voltage exceeds a predetermined level.

12. The apparatus of claim 12 in which said predetermined voltage level is 0.1 volt.

13. The apparatus of claim 11 further comprising an automatic gain circuit receiving the detected waves signal and adjusting the voltage thereof to a fixed value to compensate for ultrasonic attenuation changes in the suspension, said circuit having output connection to said timer/counter.

14. In apparatus for monitoring the stability of a solids-containing suspension or the like to determine if the solids concentration thereof has altered from a desired value due to settlement of solids within the suspension which operates to transmit ultrasonic waves through a suspension column confined in a container from a location at one side of the container and detects at the other side of the container the waves after they have passed through the suspension column and converts the detected waves to electrical signals, a method of utilizing such signals to visually display the solids concentration of the suspension, comprising the steps of:

providing a graphic plotting means, processing the electrical signals to provide time-of-flight values of the waves in passing through the suspension, processing said time-of-flight values in a computer programmed with the formula:

*Solids Conc.$_1$ = A·TOF$_1$ + B.* wherein TOF is the time-of-flight in microseconds, A is a slope calibration factor and B is an intercept calibration factor, the said A and B factors being determined from a plot of the concentration versus TOF for stable samples of known concentration along respective Y and X axes of said plot, A being the slope of the best fit straight line to stable samples TOF values, B being the concentration value where said best fit line intercepts the Y axis to obtain output data indicative of soloids concentration values, and controlling the operation of the graphic plotting means with said output data to generate a plot of the solids concentration values.

* * * * *

UNITED STATES PATENT AND TRADEMARK OFFICE
CERTIFICATE OF CORRECTION

PATENT NO. : 4,770,042

DATED : September 13, 1988

INVENTOR(S) : Wesley N. Cobb

It is certified that error appears in the above-identified patent and that said Letters Patent is hereby corrected as shown below:

On the face page, under OTHER PUBLICATIONS insert:

--"Technique To Measure Emulsion Creaming By Velocity of Ultrasound" by Howe et al., J. Dispersion Science and Technology, 7(2), 231-243 (1986) (Rec'd. Oct. 7, 1985).-- and

--"Ultrasonic Technique For Dispersed-Phase Holdup Measurements" by Bonnet et al., Ind. Eng. Chem. Res. 1987 (received for review August 20, 1985, accepted November 3, 1986), 26, 811-815.--

| | |
|---|---|
| Column 5, line 13, | "a submerged" should be --at submerged--; |
| Column 6, line 40, | "know" should be --known--; |
| Column 7, line 17, | "made by made" should be --may be made--; |
| Column 7, line 53, | "exits" should be --exists--; |
| Column 7, line 64, | "absicssa" should be --abscissa--; |
| Column 8, line 38, | "Claim 12" should be --Claim 11--; and, |

UNITED STATES PATENT AND TRADEMARK OFFICE
CERTIFICATE OF CORRECTION

PATENT NO.  :   4,770,042

DATED       :   September 13, 1988

INVENTOR(S) :   Wesley N. Cobb

It is certified that error appears in the above-identified patent and that said Letters Patent is hereby corrected as shown below:

Column 10, line 1, "soloids" should read -- solids --.

Signed and Sealed this

Fourteenth Day of March, 1989

*Attest:*

DONALD J. QUIGG

*Attesting Officer*       *Commissioner of Patents and Trademarks*